United States Patent
Durrant et al.

(10) Patent No.: US 9,090,871 B2
(45) Date of Patent: Jul. 28, 2015

(54) CELL-MEDIATED IMMUNOASSAYS

(75) Inventors: Ian Durrant, Stoke Mandeville (GB); Toni Day, East Hendred (GB); Aisling O'Keeffe, Kidlington (GB); Maxine Bampton, Abingdon (GB)

(73) Assignee: Oxford Immunotec Limited, Abingdon, Oxfordshire (GB)

( * ) Notice: Subject to any disclaimer, the term of this patent is extended or adjusted under 35 U.S.C. 154(b) by 208 days.

(21) Appl. No.: 13/253,598

(22) Filed: Oct. 5, 2011

(65) Prior Publication Data

US 2012/0028277 A1 Feb. 2, 2012

Related U.S. Application Data

(63) Continuation-in-part of application No. 13/084,980, filed on Apr. 12, 2011, now abandoned, which is a continuation-in-part of application No. 12/419,068, filed on Apr. 6, 2009, now abandoned, which is a continuation-in-part of application No. PCT/GB2007/003800, filed on Oct. 5, 2007.

(30) Foreign Application Priority Data

Oct. 6, 2006 (GB) .................................. 0619853.5

(51) Int. Cl.
| | |
|---|---|
| C12N 5/00 | (2006.01) |
| C12N 5/02 | (2006.01) |
| A01N 1/02 | (2006.01) |
| G01N 33/50 | (2006.01) |
| G01N 33/569 | (2006.01) |
| G01N 33/68 | (2006.01) |

(52) U.S. Cl.
CPC ............ *C12N 5/0087* (2013.01); *A01N 1/0205* (2013.01); *A01N 1/0231* (2013.01); *G01N 33/505* (2013.01); *G01N 33/56972* (2013.01); *G01N 33/6863* (2013.01)

(58) Field of Classification Search
None
See application file for complete search history.

(56) References Cited

U.S. PATENT DOCUMENTS

| | | | |
|---|---|---|---|
| 7,575,870 B1 | 8/2009 | Lalvani et al. | |
| 2003/0185817 A1 | 10/2003 | Thomas et al. | |
| 2010/0035283 A1 | 2/2010 | Durrant et al. | |
| 2011/0201031 A1* | 8/2011 | Durrant et al. | ............... 435/7.24 |

FOREIGN PATENT DOCUMENTS

| | | |
|---|---|---|
| JP | H11-142401 A | 5/1999 |
| WO | WO95/28643 | 10/1995 |
| WO | WO98/23960 | 6/1998 |
| WO | WO-2006/011681 A1 | 2/2006 |

OTHER PUBLICATIONS

U.S. Appl. No. 12/419,068, filed Apr. 6, 2009.
U.S. Appl. No. 13/084,980, filed Apr. 12, 2011.
Arend et al., "Detection of active tuberculosis infection by T Cell responses to early-secreted antigenic target 6-kDA protein and culture filtrate Protein 10", *The Journal of Infections Diseases*, 2000, 181:1850-1854.
Celluzzi et al., "A simple cryopreservation method for dendritic cells and cells used in their derivation and functional assessment", *Transfusion*, 2003, 43(4):488-94.
Cemerski et al., Oxidative-stress-induced T lymphocyte hyporesponsiveness is caused by structural modification rather than proteasomal degradation of crucial TCR signalling molecules, *Eur. J. Immunol.*, 2003, 33: 2178-2185.
Janetzki et al., "Standardization and validation issues of the ELISPTO Assay", *Methods in Molecular Biology*, vol. 302, 2012.
Klinman et al., "ELISPOT assay to detect cytokine-secreting murine and human cells", *Current Protocols in Immunology*, 2001, 6: Unit 6.19.
Lalvani et al., "Rapid effector function in $CD8^+$ memory T cells", *J. Exp. Med*, 1997, 186(6):859-865.
Lewalle et al., "Freezing of dendritic cells, generated from cryopreserved leukaphereses, does not influence their ability to induce antigen-specific immune responses or functionally react of maturation stimuli", *J. Immuno. Methods*, 2000, 240(1-2):69-78.
Malmberg et al., "Inhibition of activated/memory ($CD45RO^+$) T cells by oxidative stress associated with block of NF-κB activation", *The Journal of Immunology*, 2001, 167: 2595-2601.
Meier et al. "Sensitivity of a new commercial enzyme-linked immunospot assay (T SPOT-TB) for diagnosis of tuberculosis in clinical practice", *Eur. J. Clin. Microbiol. Infect. Dis.*, 2005, 24:529-36.
Peters et al. "Isolation of subsets of immune cells", *Methods in Mol. Biol.*, 2005, 32: 95-115.
Saxton et al., "Effect of ex vivo storage on human peripheral blood neutrophil expression of CD11b and the stabilizing effects of Cyto-Chex", *Journal of Immunological Methods*, 1998, 214: 11-17.
Schmielau et al., "Activated granulocytes and granulocyte-derived hydrogen peroxide are the underlying mechanism of suppression of T-cell function in advanced cancer patients", *Cancer Research*, 2001, 61: 4756-4760.
Schmitz et al. "Quantification of antigen-reactive T cells by a modified ELISPOT assay based on freshly isolated blood dendritic cells", *J. Clin. Lab. Ana.*, 2000, 16(1):30-6.
Schoorl et al., "Time dependent increase of differential monocyte count on the sysmex NE-800", *Clin. Lab. Haem.*, 1998, 20:165-168.
Stem Cell Technologies "Human CD19 selection cocktail" *Product Information Sheet*, 2004, 1-2.
Stem Cell Technologies "Human B cell enrichment cocktail", *Product Information Sheet*, 2005, 1-2.
Weinberg et al. "Effect of shipment, storage, anticoagulant, and cell separation on lymphocyte proliferation assays for human immunodeficiency virus-infected patients", *Clin. Diag. Lab. Immuno.*, 1998, 5(6):8047.

(Continued)

*Primary Examiner* — Michail Belyavskyi
(74) *Attorney, Agent, or Firm* — Choate, Hall & Stewart, LLP; Charles E. Lyon; Elizabeth M. Rohlfs

(57) ABSTRACT

A method of performing an immunologic evaluation of a subject, comprising collecting a whole blood sample from the subject, maintaining the sample for at least 6 hours after collection, purifying a population of cells comprising lymphocytes and antigen presenting cells from the maintained sample, optionally by a process incorporating a positive or negative affinity selection step to remove granulocytes, and using the purified cells in a cell-mediated immunoassay (CMI assay).

32 Claims, 1 Drawing Sheet

(56) References Cited

OTHER PUBLICATIONS

Arvinte, T. et al., Low-pH association of proteins with the membranes of intact red blood cells, II. Studies of the mechanism, Biochimica et Biophysica Acta, 981(1):61-8 (1989).

Chang, P.S. et al., Magnetic bead isolation of neutrophil plasma membranes and quantification of membrane-associated guanine nucleotide binding proteins, Analytical Biochemistry, 325(2):175-84 (2004).

Gunzer, M. et al., Two-step negative enrichment of CD4+ and CD8+ T cells from murine spleen via nylon wool adherence and an optimized antibody cocktail, Journal of Immunology Methods, 258(1-2):55-63 (2001).

Hensleigh, P.A. et al., Human T lymphocyte differentiation antigens: effects of blood sample storage on Leu antibody binding, Cytometry, 3(6):453-5 (1983).

López, J.A. et al., Single step enrichment of blood dendritic cells by positive immunoselection, Journal of Immunology Methods, 274(1-2):47-61 (2003).

McKenna, K.C. et al., Delayed Processing of Blood Increases the Frequency of Activated CD11b+ CD15+ Granulocytes which Inhibit T Cell Function, Journal of Immunological Methods, 341: 68-75 (2009).

Murphy, K. et al., Janeway's Immunobiology, 7th Edition, Garland Science, pp. 57, 228-229, and 811 (2008).

Nagasawa, M. and Yada, J., Lymphocyte Subgroup Analysis using Flow Cytometry Methods and Methods for Interpretation Thereof, Japanese Journal of Clinical Immunology, 15(6):642-646 (1992).

Nakatsui, Y. et al., Influence of Storage Conditions on Flow Cytometric Detection of Cell Surface Antigens in Acute Leukemia, The Japanese Journal of Pediatric Hematology, 19(4):209-13 (2005).

No author known, Frequently asked questions ELISPOT [online], U CyTech Biosciences, 7 pages [retrieved on Nov. 21, 2014], Retrieved from the Internet: <URL: https://www.ucytech.com/faq>.

No author known, T SPOT TB training guide [online], Oxford Immunotech, 33 pages [retrieved on Nov. 21, 2014], Retrieved from the Internet: <URL: http://oxfordimmunotec.com/north-america/wp-content/uploads/sites/2/Training-Guide-TB-US-V1.pdf>.

Schakel, K. et al., A novel dendritic cell population in human blood: one-step immunomagnetic isolation by a specific mAb (M-DC8) and in vitro priming of cytotoxic T lymphocytes, European Journal of Immunology, 28(12):4084-93 (1998).

Sleasman, J.W. et al, Immunomagnetic selection of purified monocyte and lymphocyte populations from peripheral blood mononuclear cells following cryopreservation, Clinical and Diagnostic Laboratory Immunology, 4(6):653-8 (1997).

\* cited by examiner

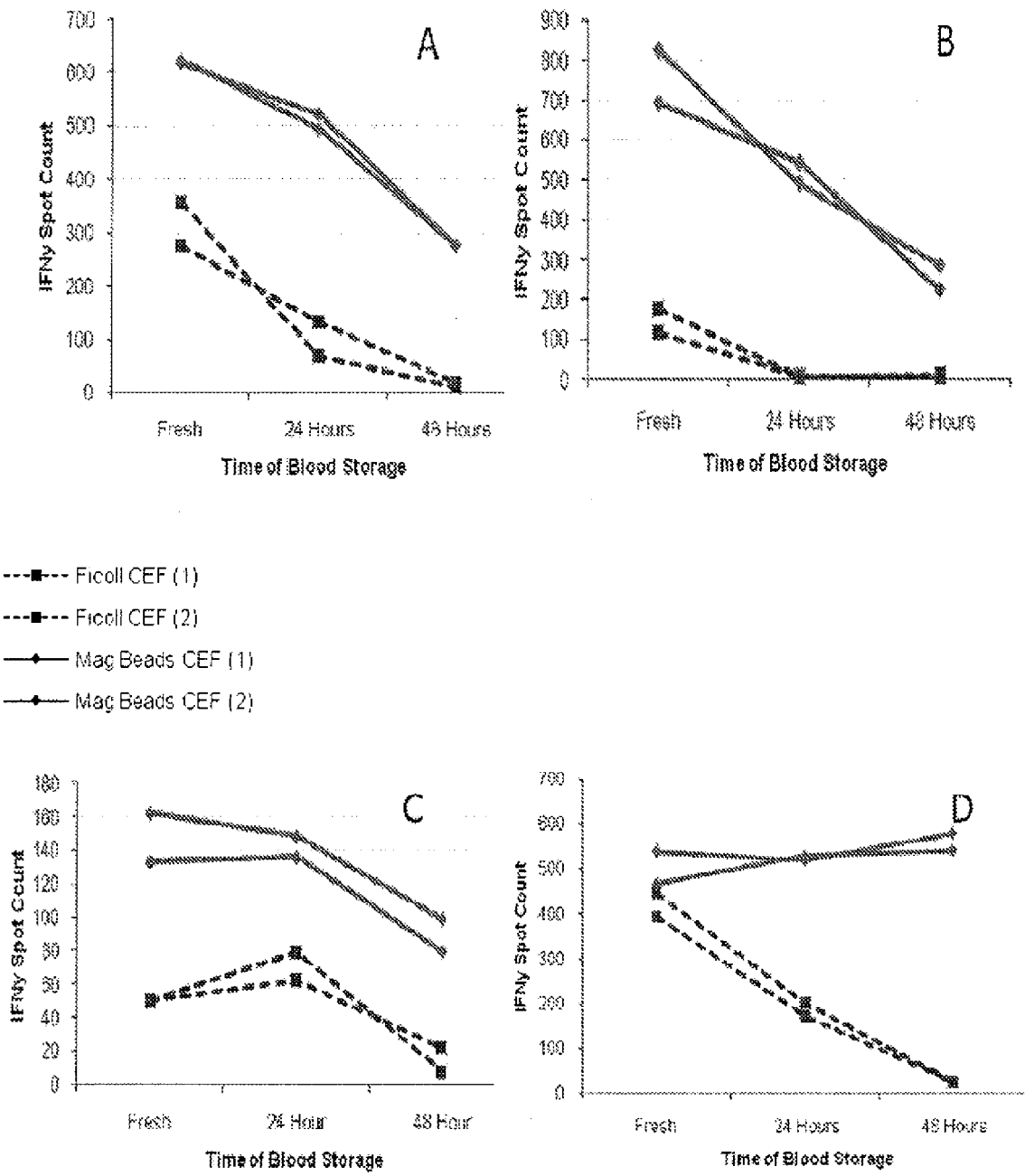

CELL-MEDIATED IMMUNOASSAYS

CROSS-REFERENCE TO RELATED APPLICATIONS

The present application is a continuation in part of U.S. application Ser. No. 13/084,980, filed Apr. 12, 2011, pending, which is a continuation in part of U.S. application Ser. No. 12/419,068, filed Apr. 6, 2009, abandoned, which is a continuation in part of International Patent Application No. PCT/GB2007/003800, filed Oct. 5, 2007, published on Apr. 10, 2008 as International Patent Publication No. WO 2008/041004, which claims priority to Application No. GB 0619853.5, filed Oct. 6, 2006, all of which applications are incorporated herein in their entireties.

FIELD OF THE INVENTION

The present invention relates to methods for storing and purifying cells from a whole blood sample, e.g., a whole blood sample. In particular, the invention relates to methods for storing and purifying cells from blood samples, such that a population of lymphocytes and antigen presenting cells is effectively stabilised and purified for use in assays which measure cell mediated immune responses in vitro.

BACKGROUND TO THE INVENTION

Cell Mediated Immune (CMI) responses are commonly used to define the immune status of an individual. Typically, in the art of clinical immunology, the term CMI response encompasses in vivo skin testing, lymphocyte proliferation assays, and the in vitro detection of cytokines produced by peripheral blood mononuclear cells (PBMC) in the presence of a specific antigen. The invention described herein addresses improved methods for manipulating, stabilising and preparing cells derived from isolated whole blood samples for use in assay techniques designed to measure one class of CMI responses, namely the in vitro cytokine-based CMI response to a specific antigen (hereinafter referred to as a "CMI Assay").

The cells of the immune system are capable of producing immune effector molecules such as cytokines following stimulation by an antigen. CMI Assays involve incubating a cell sample with an antigen and measuring for the presence or quantity of an immune effector molecule such as a cytokine to provide an indication of the ability of the individual to generate a cell-mediated immune response to the selected antigen. Cells for use in a CMI Assay also include isolated populations of lymphocytes (particularly T Cells) and Antigen Presenting Cells (APCs). APCs are involved in processing the antigen in order that the latter may be recognised by T Cell receptors located on the surface of each T Cell. Antigen-induced cytokines may be released into the assay medium and detected directly by, for example, ELISA methods, or quantified in terms of the frequency of cytokine-secreting T Cells using ELISPOT methods.

The filter immunoplaque assay, otherwise called the enzyme-linked immunospot assay (ELISPOT), was initially developed to detect and quantitate individual antibody-secreting B cells. At the time it was developed, the technique provided a rapid and versatile alternative to conventional plaque-forming cell assays. Recent modifications have improved the sensitivity of the ELISPOT such that cells producing as few as 100 molecules of a specific protein per second can be detected. These assays take advantage of the relatively high concentration of a given proteinaceous cell product (such as a cytokine) in the environment immediately surrounding the protein-secreting cell. These cell products are captured and detected using high-affinity antibodies. The ELISPOT assay has been reviewed in Current Protocols in Immunology (1994; Pub. John Wiley & Sons, Inc.), Unit 6.19 pages 6.19.1-8.

The ELISPOT assay typically involves six steps: (1) coating a purified cytokine-specific antibody to a membrane-backed microtiter plate; (2) blocking the plate to prevent non-specific absorption of any other proteins; (3) incubating the cytokine-secreting cells with appropriate reagents; (4) removal of cells and reagents; (5) adding a labelled second anti-cytokine antibody; and (6) detecting the antibody-cytokine complex on the membrane.

Methods for isolating subsets of immune cells for analysis using ELISPOT assays have previously been disclosed. See Peters et al., Methods in Molecular Biology, Handbook of ELISPOT: Methods and Protocols (2005), 302, pp. 95-115. Current methods to prepare cells from a whole blood sample for use in a CMI assay involve the isolation of peripheral blood mononuclear cells (PBMCs) using density separation methods such as a Ficoll gradient. In accordance with these methods, and in order to be effective in the CMI assay, lymphocytes and APCs must be purified from the whole blood sample as soon as possible, and in particular within 8 hours of collection of the blood sample from an individual. Janetzski, S. et al., Chapter 4: "Standardisation and Validation Issues of the ELISPOT assay", in Handbook of ELISPOT (Ed. A. E. Kalyuzhny; Humana Press, New Jersey; 2005), page 80, Note 5. This latter observation was confirmed by Meier et al., who showed that the number of spot-forming T cells as measured in a CMI assay diminished significantly following storage of isolated blood for 1-2 days. Meier et al., Eur. J. Clin. Microbial. Infect. Dis. (2005), 24, pp. 529-536; see Figure 2 in particular.

Several authors have suggested that granulocytes impair T cell function. In 1998, Saxton and Pockley examined the expression of the activation marker CD11b on neutrophils (a type of granulocyte) present in whale blood isolated from healthy laboratory volunteers. Following incubation at Room Temperature (RT) and 4° C., these authors showed that expression of the CD11b antigen by peripheral blood neutrophils was up-regulated after relatively short periods of in vitro incubation. Saxton and Pockley, J. of Immunological Methods (1998) 214:11-17 and Bartels and Schoorl, Clin. Lab. Haem (1998) 20, 165-168 also examined granulocyte activation and degranulation following storage of whole blood isolated from 20 subjects, using CD63 and CD67 granulocyte degranulation markers, and demonstrated an increase in mean CD63 and CD67 antigen expression following blood storage. Bartels and Schoorl also showed that, following whole blood incubation, granulocytes 'shift' into the monocyte region of a blood cell scattergram, as defined by the Sysmex NE-8000 haematology analyser used in these studies. Bartels and Schoorl, Clin. Lab. Haem (1998) 20: 165-168.

Other studies have provided evidence suggesting that: (a) when activated, granulocytes can be responsible for inhibiting T cell function; (b) the release of reactive oxygen species during the activation of granulocytes contributes to T cell dysfunction; and (c) a crucial T cell-signalling molecule, namely $p56^{lck}$ (a tyrosine kinase), is degraded following exposure of T cells to activated granulocytes. Schmielau & Finn Cancer Research (2001) 61: 4765-4760; Malmberg et al., The Journal of Immunology (2001) 167:2595-2601; and Cemerski et al., Eur. J. Immunol. (2003) 33:2178-2185. Cemerski et al. summarized the state-of-the-art in 2003 by pointing out (see Cemerski et al., Introduction) that reactive oxygen species were known to affect protein structure by inducing various side chain modifications on cysteines, tyrosines, methionines, prolines, etc., by forming protein cross-linkages, and by oxidising the protein backbone, resulting in protein fragmentation. Collectively, these observations indicate that T cell function in stored blood samples is likely to be impaired when measured in a CMI assay.

BRIEF DESCRIPTION OF THE DRAWING

FIG. 1 shows IFNγ ELISpot responses (duplicate) to CEF peptide from cells isolated by (i) Negative Affinity Selection with CD15 Magnetic Beads (shown by a solid line marked with diamonds: ──♦──, and (ii) Ficoll separation (shown by a broken line marked with squares: ---■--- from four different donors (A to D).

SUMMARY OF THE INVENTION

The present inventors have identified methods of maintaining or storing a whole blood sample, then purifying, from the blood sample, a population of lymphocytes and APCs for use in a cell-mediated immunoassay (CMI assay), such as an ELISPOT assay. Methods are also identified for treating whole blood samples prior to storage. These methods allow whole blood samples to be maintained, for example, for at least 6 hours, such as up to 48 hours before use in a CMI assay, such as an ELISPOT assay.

In accordance with the present invention, there is provided a method of storing and purifying cells from a whole blood sample collected from a subject, comprising storing the sample for at least 6 hours after collection, then purifying a population of lymphocytes and APCs from the stored sample, in order to remove granulocytes, for use in a CMI assay, by a process incorporating a positive or a negative affinity selection step.

In accordance with another aspect of the present invention, there is provided a method of treating and storing a whole blood sample collected from a subject, comprising treating said whole blood sample by dilution with cell growth medium; and storing the treated whole blood sample for at least 6 hours after collection, wherein after storage a population of lymphocytes and APCs can be obtained from the sample for use in a CMI assay. After storage, PBMCs or a suitable preparation of lymphocytes and APCs can be isolated from the diluted whole blood sample for use in a CMI assay, such as an ELISPOT assay.

In another aspect of the present invention, there is provided a method of 'rescuing' or maintaining the antigen- (or peptide) specific cytokine response of isolated T cells derived from a whole blood sample in an ELISPOT assay, comprising separating a population of cells comprising T cells and APCs from said whole blood sample using a positive or negative affinity selection.

In a further aspect of the present invention, there is provided a method of preparing lymphocytes and APCs suitable for use in an ELISPOT assay, wherein said method comprises removing red blood cells by filtration.

In some embodiments, the whole blood sample collected from a subject and the cells purified from the whole blood sample are not subject to conditions sufficient to effect differentiation of precursor effector T cells (or memory T cells) in the sample or the purified cells to immediate effector T cells before or during a CMI assay (e.g., an ELISPOT assay). Accordingly, detection of antigen-specific cytokine production in the CMI assay using these purified cells indicates the presence of antigen-specific immediate effector T cells in the subject.

Thus, in a preferred non-limiting embodiment, the present invention provides for a method of detecting antigen-specific immediate effector T cells in a subject, comprising (a) collecting a whole blood sample from the subject, (b) storing the sample for at least 6 hours after the collection, wherein storage may optionally include or embody shipment or transport of the whole blood sample, (c) purifying a population of cells comprising lymphocytes (e.g., T cells) and antigen presenting cells from the stored sample by a process selected from the group consisting of positive affinity selection and negative affinity selection in order to remove granulocytes, (d) contacting the purified cells with a surface carrying an immobilized antibody to a cytokine, (e) presenting to the purified cells an activating amount of the antigen in the absence of any antigen presenting cells pre-cultured with the antigen, (f) incubating the purified cells under conditions to permit release of the cytokine but where the incubation time is not sufficient to effect differentiation of precursor effector T cells (or memory T cells) to immediate effector T cells, and (g) detecting the cytokine released in response to the antigen and bound to the immobilized antibody, wherein the whole blood sample and the purified cells are not subject to conditions sufficient to effect differentiation of precursor effector T cells (or memory T cells) to immediate effector T cells before the incubation. An advantage of this method is that the interval between collection of the blood sample and purifying the lymphocytes and antigen presenting cells may be greater than 6 hours, or greater than 8 hours, or greater than 12 hours or greater than 24 hours, and up to 48 hours.

DETAILED DESCRIPTION OF THE INVENTION

The present invention provides a method of storing and purifying cells from a whole blood sample collected from a subject for use in a CMI assay such as an ELISPOT assay. The present invention also provides a method of treating a whole blood sample by dilution with cell growth medium and storing the treated whole blood sample. The method yields a sufficient level of peptide-specific cytokine response from purified or isolated lymphocytes (in the presence of APCs) from said blood sample to be detected in a CMI assay such as an ELISPOT assay, and preferably to be useful in a diagnostic or monitoring method. The subject may have been previously exposed to the peptide (or antigen).

In accordance with the present invention, a cell mediated immunoassay (CMI assay) refers to an in vitro assay to measure the cytokine-based cell mediated immune response to a specific antigen in which the presence of cells other than lymphocytes and antigen presenting cells is undesirable. Non-limiting examples of CMI assays include cytotoxic-T-lymphocyte assays, tetramer staining, proliferation assays, intracellular cytokine staining assays, ELISA assays, and ELISPOT assays. Such an assay uses a sample obtained from an individual or a subject, wherein the sample comprises cells of the immune system. The cells of the immune system are capable of producing immune effector molecules such as cytokines following stimulation by an antigen. Such assays include incubating the sample with an antigen and measuring for the presence or quantity of the immune effector molecules such as cytokines to perform an immunologic evaluation of the subject or to provide an indication of the ability of the subject to generate a cell mediated immune response to the selected antigen. In accordance with the present invention, the CMI assay is preferably an ELISPOT assay. Cells for use in the CMI assay such as an ELISPOT assay include isolated populations of lymphocytes and APCs, such as a population of T cells and APCs.

A whole blood sample collected from a subject previously exposed to a specific antigen (for example, a peptide derived from a virus) frequently contains antigen-specific effector T cells (also known as antigen-specific immediate effector T cells) that are capable of producing cytokines (following re-exposure in vitro to the same antigen) without first undergoing cell division or differentiation. Such a sample is also likely to contain antigen-specific memory cells that cannot produce cytokines (following re-exposure to antigen) without further differentiation to immediate effector T cells. When re-exposed in vitro to the same antigen, these antigen-specific memory T cells (also known as precursor effector T cells) can divide and differentiate to immediate effector T cells.

Particular types of ELISPOT assays have been developed for detecting antigen-specific cytokine responses by immediate effector T cells from a subject previously exposed to the antigen. Typically, these cells have already been exposed to the specific foreign antigen in vivo, and, when re-exposed to the same 'cognate' antigen ex vivo, their cytokine response is triggered very rapidly (e.g., within 6 hours of in vitro exposure of the cells to the antigen)—that is, the antigen-specific T cell response is not dependent on cell division or differentiation. Such ELISPOT assays have been previously described in, for example, Lalvani et al., 1997, *J. Exp. Med*, 186:859-65 and International Patent Application No. PCT/GB97/03222, published on Jun. 4, 1998 as International Patent Publication No. WO 98/23960, and U.S. Pat. No. 7,575,870. In these assays, cells isolated from a subject are incubated with the antigen under conditions (e.g., an incubation time period of 16-20 hours) insufficient to effect differentiation of memory T cells or precursor effector T cells to immediate effector T cells such that the detection of antigen-specific cytokine release indicates the presence of antigen-specific immediate effector T cells in the subject.

Other types of CMI assays include whole blood assays, where, following specific antigen stimulation ex vivo, cytokine released from T cells present in whole blood is measured in isolated plasma using standard ELISA techniques (e.g., Arend et al., 2000, *J. Infect. Dis.*, 181:1850-54).

The isolated preparation of lymphocytes and APCs, in particular T cells and APCs, prepared from a whole blood sample in accordance with the present methods provides a preparation that can be used in a CMI assay such as an ELISPOT assay for use in diagnosis or monitoring. Such a preparation generates responses sufficient to allow diagnosis, or for other purposes, for example, monitoring the progress of, or resistance to, a chronic infectious disease in the subject, and monitoring induction and maintenance of antigen-specific T cells following immunization of the subject with a vaccine. Such responses may be defined as 50% higher than background. Alternatively, such responses may be defined as being at least 50% of the maximal response that can be obtained using a freshly isolated whole blood sample.

For example, in a typical assay, $2.5 \times 10^5$ viable PBMCs may be used per well in an ELISPOT assay. In an ELISPOT assay for tuberculosis, typically, a negative control will have less than 5 spots. In this case, a positive or reactive sample will have 6 or more spots more than the negative control. If the negative control has 6 or more spots, a reactive sample is indicated if it contains more than two times the negative control spot count.

In one embodiment, the methods of the present invention use a positive affinity selection step or a negative affinity selection step to remove granulocyte cells from a whole blood sample, before or after storage. A positive affinity selection step is used to bind those cells of interest to a solid support and thus separate bound cells from non-bound cells. The purified bound cells are retained, and the non-bound cells are discarded.

In the alternative, a negative affinity selection step is used in order to remove those cells which are not required or undesirable in the cell preparation (e.g., granulocytes) for use in the CMI assay, such as an ELISPOT assay. Thus the cells bound to the solid support are discarded and the purified unbound cells are recovered and retained.

The method will result in purification of both lymphocytes (such as T cells) and APCs. The purification may comprise positive or negative affinity selection of both lymphocytes and APCs, in which case there will typically be an enrichment in the sample of both of these cell types, i.e. both the ratio of T cells to total number of cells and the ratio of APCs to total number of cells will increase in the sample as a result of carrying out the method of the invention.

In accordance with one aspect of the invention, the whole blood sample is maintained or stored before purifying cells from the whole blood sample by a method or process including a positive or negative affinity selection step. For example, the whole blood sample may be stored prior to isolation of the selected cell population. After storage for at least 6 hours, or at least 8 hours, up to 10, 12, 18, 24, 36 or 48 hours, the whole blood sample is treated (i.e. subjected to the affinity selection) to isolate the selected cell population, which can then be used in the CMI assay, such as an ELISPOT assay. In the alternative, the whole blood sample is treated (i.e., subjected to the affinity selection) shortly after it has been obtained, for example, within 1 hour, up to 6 hours, or up to 8 hours after it has been obtained to isolate the selected cell population. Such a cell population is then used in the CMI assay, such as the ELISPOT assay.

Preferably, the whole blood sample is stored between −5° C. and 40° C., typically between 2° C. and 8° C. or between 18° C. and 25° C. In a particularly preferred embodiment, the whole blood sample is stored at room temperature, such as at about 18° C. or 20° C. or from 18° C. to 25° C. or from 20° C. to 25° C. Where cell division and/or differentiation (e.g., differentiation of precursor effector T cells or memory T cells to immediate effector T cells) is not desired, the whole blood sample may be kept under conditions not sufficient to effect such division and/or differentiation. For example, the whole blood sample may be maintained or stored for less than 24 hours, 16 hours or 12 hours.

It will be understood that the storage step, during which a whole blood sample is maintained for a specified combination of time and temperature, may optionally include or embody the act of physically shipping or transporting the blood sample from one geographical location to another geographical location under conditions in which the said time and temperature parameters are generally maintained. This storage mode may involve transport by road, rail, or air, and represents an important aspect of the overall storage element of the invention, since an individual whose immune status is to be analysed, and from whom a blood sample has been obtained, is often located at a considerable distance from the laboratory which undertakes the analysis, for example, by means of performing a cell-mediated immunoassay.

Typically, a whole blood sample, housed in a suitable leak-proof vessel, can be shipped inside an insulated container (e.g., a Thermosafe Insulated Shipper—VIP Model #07VIP-UPS; available from Tegrant Corporation, Arlington Heights, Ill. 60004). Optionally, devices which are capable of controlling temperature variation during shipment to within a few degrees are placed in close proximity with the blood sample. For example, the Phase 22™/20-24° C. pouch from Cryopak Corporation (available from TCP Reliable, Edison, N.J. 08837) is able to maintain contained blood samples at between 20-24° C. during shipment in hot or cold external environments. The time periods required for shipment within regions of the USA (from the point of departure of the sample to the place of its receipt) are well within the storage time periods falling within the scope of the invention. And it will be understood that the shipment time (that is, the period during which a sample is shipped from location A to location B) may represent all of part of the storage or maintenance period as specified in the invention.

The shipped blood sample is removed from the storage container at the destination location, then further processed to generate purified cells containing lymphocytes and antigen presenting cells in accordance with the invention.

In a further embodiment the sample is not frozen at any stage of any of the methods mentioned herein. In another embodiment the sample is not frozen between the stages of being taken or collected from the individual and being stored and purified (by a method of the invention); and/or the purified cells from the sample are not frozen between the stages of being stored and purified and being used in a CMI assay.

In one aspect of the present invention, the purification method comprises a negative affinity selection step to remove granulocytes and optionally red blood cells from the whole blood sample in order to obtain the preparation of lymphocytes and APCs for use in an ELISPOT assay.

Thus, in accordance with the one aspect of the present invention, a method is provided in which both granulocytes and red blood cells are removed from the whole blood sample in a single step. In accordance with this method, the whole blood sample is contacted with an antibody preparation comprising anti-CD66b and glycophorin A antibodies. The antibodies serve to aggregate red blood cells and granulocytes. The aggregated red blood cells and granulocytes can be removed from the sample, for example by centrifugation. The sample may also be subjected to a Ficoll gradient prior to centrifugation.

In another aspect of the invention, the negative affinity selection comprises the use of a solid support having a ligand bound thereto which binds to a cell surface protein present on the surface of granulocytes, which does not bind to cell surface proteins present on the surface of lymphocytes and APCs used in the ELISPOT assay. For example, a solid support can be provided comprising an anti-CD15 ligand to bind to CD15+ cells from the sample and/or anti-CD66b to remove CD66b+ cells from the sample.

In accordance with this aspect of the present invention, a whole blood sample, or a blood sample which has been treated to remove red blood cells is brought into contact with the solid support comprising an anti-CD15 ligand or anti-CD66b ligand, under conditions which allow binding of granulocytes. The preparation of lymphocytes or APCs having granulocytes removed therefrom can be obtained directly, for example by contacting the sample with the solid support and collecting any material which does not bind the solid support.

In the alternative, the solid support having granulocytes or other unwanted cells bound thereto can be separated from the remainder of the sample. For example, the solid support can comprise beads such as magnetic beads. Once the beads have been contacted with the sample and under conditions to allow binding of granulocytes to the solid support, the beads can be separated from the sample to leave a preparation of lymphocytes and APCs having granulocytes removed therefrom. In a preferred embodiment, the solid support comprises magnetic beads which can be separated from the remainder of the sample, for example by the application of a magnetic field.

It will be understood that other ligands, particularly antibodies, capable of binding to a cell surface marker on the surface of granulocytes, may be used for negative affinity selection. For example, the following antibodies may also be used to remove granulocytes by this method: anti-CD16b and/or anti-CD88.

Preferably, in accordance with this aspect of the present invention red blood cells are also removed from the whole blood sample. This can be done before, after or at the same time as removal of CD15+ expressing cells or granulocytes.

Red blood cells can be removed from the sample by any suitable method. For example, red blood cells in the sample may be removed by lysis of the red blood cells (Simon et al., Immunol. Commun. 1983, Vol. 12, pp. 301-314).

In accordance with one aspect of the invention, red blood cells are removed by filtration. In accordance with this aspect of the invention, a method is provided for preparation of lymphocytes and APCs for use in a CMI assay such as an ELISPOT assay which comprises filtration to remove red blood cells. Such methods can be used on their own or with one or more of the other methods of the invention, such as negative affinity selection with anti-CD15+ ligands to remove granulocytes.

The filtration methods of the present application include applying a whole blood sample to a filter. The filters are selected such that red blood cells pass through the filter while lymphocytes and APCs are retained on the filter. In accordance with this method, the filters having lymphocytes and APCs thereon can be used directly in the CMI assay such as the ELISPOT assay. Alternatively, the lymphocytes and APCs can be collected, for example by washing the filter or back flushing the filter and collecting the recovered lymphocytes and APCs.

In accordance with another aspect of the present invention, a preparation of lymphocytes and APCs are purified from a whole blood sample by a method involving a positive affinity step, wherein optionally the affinity selection step selects all types of T cells (for example irrespective of whether they are CD4 or CD8 or irrespective of the epitope which they recognize).

In one aspect, the whole blood sample is contacted with a solid support having attached thereto ligands which bind to cell surface proteins present on the surface of the lymphocytes and APCs. The ligands may be antibodies.

In a preferred aspect of the present invention, such ligands are selected from anti-CD4, anti-CD8, anti-CD19, anti-CD45, anti-CD45RC and anti-CD14 ligands. For example, a solid support can be provided to bind to CD4+, CD8+ CD14+ and CD19+ cells in the whole blood sample or a subset such as CD4+, CD8+ and CD19+ cells. Isolation of such cells provides a preparation of lymphocytes and APCs which are suitable for use in the ELISPOT assay. Such a preparation may encompass a mixture of CD4+ and CD8+ T lymphocytes, B cells and monocytes. In one embodiment, anti-CD4 and/or anti-CD8 ligands are not used in the purification step, and preferably anti-CD4 antibodies and/or anti-CD8 antibodies are not used in the purification step.

In a preferred embodiment, the ligands on the solid support are selected so that undesirable cells in the final preparation, such as granulocytes, are not retained on the solid support. For example, the ligands are selected so that they are specific for lymphocyte and APCs and do not bind to granulocytes. The solid support can be provided with anti-CD4, anti-CD8 and anti-CD19 ligands or other appropriate ligands in approximately the same ratios. Alternatively, the ratio of each individual ligand can be selected, for example to reflect the proportion of each cell present in whole blood. In the alternative, the ratio of ligands, such as CD4:CD8:CD19 ligands can be selected to bind and isolate lymphocytes and APCs in a desired ratio, such as one particularly suitable for use in an ELISPOT assay.

Methods of affinity selection using solid supports having ligands bound thereto to bind to selected proteins are well known in the art. In general, a whole blood sample is brought into contact with the solid support comprising the ligands of interest, under conditions which allow binding of cells to the ligands via the relevant cell surface protein. The solid support can be separated from the remainder of the sample in order to separate bound cells from non-bound material. Washing steps may be included, for example to rinse non-bound material from the solid support.

In a preferred aspect of the present invention, the solid support comprises magnetic beads. Such magnetic beads can easily be separated from a sample, for example by the application of a magnetic field. Where the solid support is provided in the form of magnetic beads or other types of bead, each bead may have a single ligand present thereon, such as anti-CD4 ligand. Beads which individually carry each ligand, such as anti-CD4, anti-CD8, anti-CD14 or anti-CD19 can be combined together to produce a solid support which will bind to the desired cells, such as CD4+, CD8+, CD14+ and CD19+ cells. In the alternative, each magnetic bead may be provided with more than one ligand such as both anti-CD4 and anti-CD8 ligands or anti-CD4 and anti-CD19 ligands or a combination of all ligands. In a particularly preferred embodiment, the ratio of ligands, such as anti-CD4: anti-CD8: anti-CD19 is selected to correlate to the ratio of lymphocytes and APCs desired in the final preparation for use in a CMI assay (for example, an ELISPOT assay). The quantity of magnetic beads can also be selected in order to isolate a selected number of cells, to facilitate further processing of the preparation for use in the CMI assay.

The preparation of selected cells, and in particular lymphocytes and APCs that are bound to the solid support can be used in an assay directly. In particular, magnetic beads having bound thereto the relevant cells can be used in a CMI assay, such as an ELISPOT assay. Preferably, the beads having cells bound thereto are washed prior to use in the assay. In the alternative, once the selected cells have been isolated from the remainder of the whole blood sample, the cells bound to the solid support can be dissociated or separated from the solid support for use in the assay.

In accordance with another non-limiting embodiment of the present invention, which may or may not include an affinity selection step, a whole blood sample is treated by dilution with cell growth medium and stored before being used in the CMI assay such as an ELISPOT assay. The diluted whole blood sample can be stored for at least 6 hours after collection for example for at least 8 hours after collection from an individual, preferably up to 10, 12, 18, 24, 36 or 48 hours after collection. Where cell division and/or differentiation (e.g., differentiation of precursor effector T cells or memory T cells to immediate effector T cells) is not desired, the treated whole blood sample may be kept under conditions not sufficient to effect such division and/or differentiation. For example, the whole blood sample may be maintained or stored at 2-8° C.

In accordance with this aspect of the present invention, the whole blood sample is stabilized or treated prior to storage. For example, the method comprises diluting a whole blood sample with cell growth medium, such that when the whole blood sample or an isolated preparation of T cells and APCs obtained from said stored whole blood sample is used in an ELISPOT assay up to 48 hours after collection of the sample a viable response is maintained.

In accordance with the present invention, the whole blood sample can be diluted with cell growth medium in any appropriate ratio. In a preferred embodiment, the ratio of whole blood sample to cell growth medium is 1:1. Alternatively, the ratio of whole blood sample to cell growth medium can be 2:1, 3:1, 4:1, 5:1, 6:1, 7:1, 8:1, 9:1, 10:1, up to 10:1, 20:1 or 30:1. Alternatively, the ratio of whole blood sample to cell growth medium can be 1:2, 1:3, 1:4, 1:5, 1:6, 1:7, 1:8, 1:9 or 1:10, up to 1:15, 1:20 or 1:30.

In accordance with one embodiment, the diluting medium is added to the whole blood sample, but is not subjected to shaking or mechanical mixing. The whole blood sample is preferably stored in a standard heparinized tube. Preferably, the whole blood sample is stored in the dark.

The cell growth medium or diluting medium for use in the invention can be any appropriate cell growth medium or isotonic saline solution. For example, the medium can be a commercially available medium such as AIM-V (Invitrogen Paisley UK), or RPMI 1640™ (Sigma Aldrich Corp, St. Louis, Mo., USA). In a preferred embodiment, the cell growth medium is serum-free medium, such as AIM-V.

In accordance with one aspect of the invention said treated whole blood sample is used or prepared for use in a CMI assay after storage. Typically, a preparation of PBMCs, or T lymphocytes and APCs are purified from said treated whole blood sample after storage for use in the CMI assay. Any suitable method can be used to obtain the isolated preparation of cells for use in a CMI assay, such as an ELISPOT assay. Typically, PBMCs can be isolated, for example, using a Ficoll gradient. More preferably, red blood cells and granulocytes are removed from the treated whole blood sample, for example to isolate a preparation of lymphocytes and APCs, by a method including an affinity selection step.

Treatment by dilution may also be used in another aspect of the invention to treat an isolated preparation of lymphocytes and APCs prior to storage of the preparation before its use in a CMI assay.

In a further aspect of the invention, whole blood may be maintained or stored for several hours, preferably for at least 6 hours, or up to 12 hours, or from 12-48 hours. Such storage may be at 2-8° C., or at room temperature. Following storage, a preparation of lymphocytes and APCs may be prepared by affinity selection as described above, and optionally the peptide specific response of T cells in the preparation may be measured in a CMI assay. In this manner, the in vitro activity of T cells introduced into the CMI assay is stabilised and maintained. Accordingly, this approach reduces or obviates a marked reduction in T Cell activity in vitro which is observed in preparations of lymphocytes and APCs isolated using, for example, standard Ficoll gradients from a whole blood sample, when the blood sample is stored for several hours prior to the isolation step.

In a preferred non-limiting embodiment, the present invention provides for a method of detecting antigen-specific T cells in a subject, comprising (a) collecting a whole blood sample from the subject, (b) storing the sample for at least 6 hours after the collection, wherein storage may optionally include or embody shipment or transport of the whole blood sample, (c) purifying cells comprising lymphocytes (e.g., T cells) and antigen presenting cells from the stored sample by a process selected from the group consisting of positive affinity selection and negative affinity selection in order to remove granulocytes, (d) presenting to the purified cells an activating amount of the antigen, (f) incubating the purified cells under conditions to permit release of the cytokine, and (g) detecting the cytokine released in response to the antigen.

In a further preferred non-limiting embodiment, the present invention provides for a method of detecting antigen-specific immediate effector T cells in a subject, comprising (a) collecting a whole blood sample from the subject, (b) storing the sample for at least 6 hours after the collection, wherein storage may optionally include or embody shipment or transport of the whole blood sample, (c) purifying cells comprising lymphocytes (e.g., T cells) and antigen presenting cells from the stored sample by a process selected from the group consisting of positive affinity selection and negative affinity selection in order to remove granulocytes, (d) contacting the purified cells with a surface carrying an immobilized antibody to a cytokine, (e) presenting to the purified cells an activating amount of the antigen in the absence of any antigen presenting cells pre-cultured with the antigen, (f) incubating the purified cells under conditions to permit release of the cytokine but where the incubation time is not sufficient to effect differentiation of precursor effector T cells (or memory T cells) to immediate effector T cells, and (g) detecting the cytokine released in response to the antigen and bound to the immobilized antibody, wherein the whole blood sample and the purified cells are not subject to conditions sufficient to effect differentiation of precursor effector T cells (or memory T cells) to immediate effector T cells before the incubation.

The present invention also provides a kit for storing a whole blood sample comprising a standard heparinized tube and cell growth medium. The invention also provides a kit for carrying out an ELISPOT assay on cells which have been stored and purified by a method as disclosed herein, wherein the kit comprises:

(i) a cytokine-specific antibody, optionally attached to a microtiter plate, and
(ii) one or more of the ligands mentioned herein which can be used in affinity selection, optionally bound to a solid support, and
(iii) optionally instructions for carrying out the ELISPOT assay and/or method of storing and purifying the cells.

Further, the invention also provides a kit for purifying a population of lymphocytes and APCs according to the invention, wherein the kit comprises one or more of the ligands mentioned herein, optionally bound to a solid support. The kit may also comprise instructions for carrying out the method in accordance with the invention.

In other embodiments of the invention, the whole blood sample is treated using a positive or negative affinity selection step to isolate a population of T cells and APCs for use in the CMI assay, such as an ELISPOT assay without storing the samples. In a further embodiment, the positive or negative affinity selection methods may be used to isolate a preparation of cells for use in a CMI assay such as an ELISPOT assay, such cells being derived from whole blood samples which have been treated by dilution and stored.

Any of the above embodiments may be carried out on a sample from a human, such as a human that is suspected of having a disease which can be diagnosed or monitored by a CMI assay (for example, an ELISPOT assay).

The invention is hereinafter described in more detail by reference to the following Examples.

Example 1

Treatment by Dilution with Culture Medium

Immediately after venipuncture, one 10 ml Lithium Heparin Vacutainer (BD Biosciences, Oxford, UK) of whole blood from each of a total of 78 donors and was processed over the space of 6 months, using the T-SPOT.TB assay kit (Oxford Immunotec, Abingdon, UK). The method was carried out according to the manufacturer's instructions accompanying the kit. This method comprises: a) a standard Ficoll method for preparation of Peripheral Blood Mononuclear Cells (PBMCs)—see under Sample Collection and Preparation, Procedure 2 "alternative blood collection methods" and Note 2; b) viable cells were counted using the Trypan Blue Dye Exclusion method (Freshney, R. (1987) Culture of Animal Cells: A Manual of Basic Technique, p. 117, Alan R. Liss, Inc., New York); c) cells were diluted in GIBCO AIM-V (Invitrogen, Paisley, UK) to give 250,000 cells per 100 µl; d) 250,000 (100 µl) of the Ficoll-extracted cells were added to each microtiter plate well pre-coated with anti-gamma interferon, together with one of the following: phytohaemagglutinin (PHA) positive control; or specific test antigens from $M.$ $tuberculosis$ (Panel A; Panel B); or from cytomegalovirus/epstein barr virus/influenza virus (CEF; Mabtech, Sweden), which antigen is not provided in the T-SPOT.TB kit; e) the plate was incubated for 16 to 20 hours (37° C., 5% $CO_2$), washed four times with phosphate buffered saline (PBS) before adding an alkaline phosphatase-conjugated secondary antibody and incubating for 1 hour at 2-8° C.; f) the wells were washed four times, and 5-bromo-4-chloro-3' indoylphosphate/Nitro Blue Tetrazolium (BCIP/NBT) then added and incubated for 7 minutes. After the spots had developed, the reaction was stopped using distilled water; g) after drying at 37° C. for 4 hours, the number of spot forming cells (SFC) for each well was recorded and analysed.

The remaining blood from each donor was diluted 1:1 in AIM-V and stored at room temperature (18-25° C.) in the dark overnight for 24 hours.

On Day 2, the T-SPOT.TB assay was performed on the stored blood including the standard Ficoll method for preparation of PBMC. The T-SPOT.TB assay was then conducted to determine the SFC counts, using a positive control (PHA) and a nil control (lacking antigen). The nil control was subtracted from the test antigen well SFC count. If any of the antigen wells contained six or more spots and the nil control contains zero spots, then the sample was deemed 'reactive' for that antigen under test. The Tables below show the relationship between fresh and diluted and stored blood. Reactive and non-reactive results are shown using Panel A, Panel B and CEF wells for each donor blood sample both before and after overnight blood storage (following 1:1 dilution in AIM-V) at room temperature (RT). The percentage of the total number of donors is also indicated. CEF antigen was dissolved in AIM V, and was present in the assay at a level of 5 µg/ml.

| | Panel A Antigen | |
|---|---|---|
| | Fresh Blood | |
| Diluted/Stored Blood | Reactive | Non-Reactive |
| Reactive | 3 (3.8%) | 1 (1.3%) |
| Non-Reactive | 2 (2.6%) | 72 (92.3%) |

96.2% clinical concordance

| Panel B Antigen | | |
|---|---|---|
| | Fresh Blood | |
| Diluted/Stored Blood | Reactive | Non-Reactive |
| Reactive | 5 (6.7%) | 0 (0%) |
| Non-Reactive | 3 (4%) | 67 (89.3%) |

96% clinical concordance

| CEF Antigen | | |
|---|---|---|
| | Fresh Blood | |
| Diluted/Stored Blood | Reactive | Non-Reactive |
| Reactive | 28 (77.8%) | 0 (0%) |
| Non-Reactive | 5 (13.9%) | 3 (8.3%) |

Results demonstrate 86.1% clinical concordance (assuming that 6 spots greater than nil control indicates reactivity).

Thus, the addition of medium to the blood sample enables a positive SFC response to be measured in PBMC after 24 hours storage, a response that is similar to that seen when measured on blood processed immediately after collection. Blood collected and stored for 24 hours without the addition of medium demonstrated a significant loss in the measurable CMI response (results not shown).

Example 2

Positive Affinity Selection

On Day 1, and within 2 hours of venipuncture, two 10 ml Lithium Heparin Vacutainers of whole blood from each of nine donors were placed in storage, one in the dark at RT (18-25° C.) and the other in the fridge (2-8° C.).

At each time point, either 0-2 hours (fresh) or 24 hours (stored) post venipuncture for each donor, 3 mls of whole blood were diluted 1:1 with wash buffer (PBS/0.1% BSA/2 mM EDTA) and mixed with 80 µl of a cocktail of specific magnetic Dynabeads, namely 111.45 (CD4); 111.47 (CD8); 111.49 (CD14); and 111.43 (CD19), which were mixed in equal proportions (Invitrogen). These 'beads' positively select cells based on the presence of specific differentiation (CD) markers: CD4 and CD8 for T cell subsets; CD14 (monocytes) and CD19 (B cells and APC's). The samples were mixed at RT for 12 mins, and the beads were separated by placing sample tubes in a magnetic particle concentrator (MPC: Invitrogen, Paisley, UK) for 2 mins. The supernatant was discarded, and the beads were washed twice in PBS and then separated again on the MPC. The beads were then resuspended in 1 ml AIM-V and cells were counted using the Trypan Blue Dye Exclusion Method. Cells were diluted in AIM-V to give 250,000 cells per 100 µl.

In parallel, at each time point, either 0-2 hours (fresh) or 24 hours (stored) post-venipuncture for each donor, 5 ml of whole blood was processed immediately using the standard Ficoll method as indicated in Example 1.

All processed samples were then assayed using the T.SPOT.TB assay kit (see Example 1), using antigens CEF (5 µg/ml), or PPD (1 µg/ml), or PPD/CEF (1 µg/ml and 5 µg/ml respectively) in the assay wells, none of which are provided in the T-SPOT.TB kit; PPD (Product Code RT23) was obtained from Statens Serum Institut (Copenhagen, Denmark); for CEF, see Example 1. PPD and CEF were used to identify CD4+ and CD8+ T cells respectively.

The following Table, incorporating the average of the results for all donors, displays the SFC counts measured by ELISPOT for cells selected from fresh or stored blood using CD4, CD8, CD14 & CD19-conjugated magnetic beads compared to use of Ficoll only. The blood stored at RT for 24 hours and selected using beads has produced comparable results to the 'fresh bead' samples, and yield better results than when 'Ficoll only' samples are stored at RT, and both 'Ficoll only' and 'beads' are stored at 4° C.

| | Fresh | | Stored (24 Hours) | | | |
|---|---|---|---|---|---|---|
| Antigen | Ficoll | Beads | Ficoll (4° C.) | Ficoll (22° C.) | Beads (4° C.) | Beads (22° C.) |
| PPD | 100 | 78 | 15 | 41 | 53 | 70 |
| CEF | 100 | 194 | 13 | 45 | 111 | 149 |
| PPD/CEF | 100 | 136 | 14 | 43 | 82 | 109 |
| PPD | | 71.40 | 18.21 | 35.06 | 67.34 | 49.67 |
| CEF | | 109.20 | 18.51 | 37.24 | 87.54 | 109.40 |
| PPD/CEF | | 81.80 | 1.52 | 2.85 | 40.89 | 56.25 |

The results were normalised, assuming that 'fresh' samples, processed with Ficoll only, yield an SFC count of 100% in the ELISPOT assay. The top three rows show the mean SFC counts, and the bottom three rows show the standard deviations.

Example 3

Negative Affinity Selection

Immediately after venipuncture, two 10 ml Lithium Heparin Vacutainers of whole blood were collected from each of 4 donors over the space of 1 month.

For one sample from each donor, a negative selection step was undertaken using MACSi anti-CD15 magnetic beads (Miltenyi Biotech, Bergisch Gladbach, Germany). The beads were resuspended thoroughly before use to ensure a homogeneous dispersion. 400 µl of beads were added to 4 ml of whole blood in a 15 ml conical tube. The tubes were incubated at RT using the MACSimix (Miltenyi Biotech) tube rotator at medium speed (8 rpm) for 15 minutes. The tubes were placed in the MACSiMag separator (Miltenyi Biotech), and the beads allowed to adhere to the wall of the tube for 2 minutes. Retaining the tube in the magnet, the supernatants were removed using a pipette and retained in a fresh tube. The tubes containing the supernatants were again placed in the MACSiMag separator and any residual beads allowed to adhere to the wall of the tube for 2 minutes. Retaining the tube in the magnet, the supernatant was transferred to a 50 ml conical tube. 16 ml of freshly prepared 1× red blood cell (RBC) lysis buffer (prepared by dilution of 10× lysis buffer: 1.55M $NH_4Cl$, 100 mM $KHCO_3$, 10 mM EDTA) were added and the tubes incubated at room temperature for 5 minutes. The samples were centrifuged at 300×g for 10 minutes. The pelleted cells were washed twice in lysis buffer (5 ml) and centrifuged each time at 300×g for 5 minutes. The cells were washed once in RPMI and diluted in 1 ml of AIM-V for use in an ELISPOT assay.

In parallel with this method, and using a second sample from each donor, 5 ml of whole blood was processed by the standard Ficoll method as indicated in Example 1.

Purified PBMC samples were then assayed in the T.SPOT.TB assay, as outlined in Example 1, using CEF (5

μg/ml) as antigen for Donor 1, 2 and 4 samples; and Panel A and B antigens (33 μg/ml) for the Donor 3 samples.

The SFC count obtained with PBMCs (shown in the Tables below) prepared using a negative selection approach with MACSi anti-CD15 magnetic beads demonstrated high equivalence to those PBMCs that were prepared using Ficoll gradients. This antibody-based method of PBMC isolation proved to be technically feasible and produced highly reproducible results in the T-SPOT.TB assay.

|  | Donor 1 | | Donor 2 | |
|---|---|---|---|---|
|  | Ficoll | MACSi | Ficoll | MACSi |
| CEF | 240 | 239 | 100 | 111 |
|  | 248 | 235 | 98 | 124 |
| Mean | 244 | 237 | 99 | 117.5 |
| Std dev | 5.66 | 2.83 | 1.41 | 9.19 |

|  | Donor 3 | |
|---|---|---|
|  | Ficoll | MACSi |
| − | 0 | 0 |
| + | >100 | >100 |
| panel A | 41 | 31 |
|  | 45 | 42 |
|  | 44 | 38 |
| panel B | 179 | 99 |
|  | 157 | 106 |
|  | 151 | 83 |
|  | Mean | |
| Panel A | 43.3 | 37 |
| Panel B | 162.3 | 96 |
|  | St Dev | |
| Panel A | 2.08 | 5.57 |
| Panel B | 14.74 | 11.79 |

|  | Donor 4 | |
|---|---|---|
|  | Ficoll | MACSi |
| − | 0 | 0 |
|  | 0 | 0 |
| + | 116 | 100 |
|  | 116 | 100 |
| CEF | 187 | 240 |
|  | 210 | 214 |
|  | 180 | 189 |
|  | Mean | |
| − | 0 | 0 |
| + | 116 | 100 |
| CEF | 192.3 | 214.3 |
|  | St Dev | |
| − | 0 | 0 |
| + | 0 | 0 |
| CEF | 15.70 | 25.50 |

(N.B. For Donors 3 and 4, (−) wells indicate absence of antigen; (+) wells indicate presence of PHA (5 μg/ml).

Example 4

Negative Affinity Selection

Two separate experiments were performed, each using pooled whole blood from a group of either 15 or 11 donors.

For each experiment: a) on Day 1, immediately after venipuncture, one 10 ml Lithium Heparin Vacutainer of whole blood from each donor pool was processed according to the standard Ficoll method (see Example 1). Viable PBMC were counted using the Trypan Blue Dye Exclusion Method. Cells were diluted in cell culture medium (AIM-V) to give 250,000 cells per 100 μl; b) the remaining blood was stored in the dark, undiluted, either in a fridge at 2-8° C. or at RT (18-25° C.) for 24 hours; c) on Day 2, stored blood samples were processed according to the standard Ficoll method for PBMC preparation, and viable cells were counted and diluted as described above (see paragraph 1, this Example).

In parallel samples processed in each experiment, both on Day 1 (fresh) and Day 2 (stored) for each donor, 4.5 mls of whole blood was added to 15 ml centrifuge tubes, and 225 μl of RosetteSep (StemCell, Vancouver, BC, Canada) was then added to each tube to bind the RBC to the granulocytes using a tetramer complex containing anti-CD66b and glycophorin A antibodies. Samples were mixed gently and left to incubate for 20 minutes at RT. Samples were then diluted 1:1 with RPMI, and the PBMCs were isolated from the granulocyte-depleted cells by the standard Ficoll method (see Example 1), thus allowing the RBC and granulocytes to be separated from lymphocytes and APCs. The latter cells were then washed and processed according to the manufacturer's instructions accompanying the kit—see Example 1.

Results are shown below. In the two separate experiments performed, one used CEF (5 μg/ml) as antigen, and the other used PPD (1 μg/ml) in the assay. Top Table: CEF-induced SFC counts mean of 15 donors) for Ficoll and RosetteSep treatment at 4° C. and RT. Bottom Table: PPD-induced SFC counts (mean of 11 donors) for Ficoll and RosetteSep treatment following storage at 4° C. and RT. The results demonstrate that samples stored at 4° C. and then subjected to anti-granulocyte antibody treatment followed by Ficoll purification of PBMC are equivalent to standard 'fresh' samples, and also yield higher SFC counts than when samples are stored at RT prior to anti-granulocyte antibody treatment.

| CEF | Fresh Ficoll | Ficoll, 4° C. | RosetteSep, 4° C. | Ficoll, RT | RosetteSep, RT |
|---|---|---|---|---|---|
| Mean | 80 | 54 | 78 | 39 | 60 |
| sum | 4870 | 3252 | 4759 | 2388 | 3681 |
| % diff from fresh Ficoll | | −33.2 | −2.3 | −51 | −24.4 | n = 15 donors, 61 replicates

| PPD | Fresh Ficoll | Ficoll, 4° C. | RosetteSep, 4° C. | Ficoll, RT | RosetteSep, RT |
|---|---|---|---|---|---|
| Mean | 22.6 | 9.4 | 21.4 | 8 | 17.4 |
| sum | 722 | 301 | 685 | 256 | 558 |
| % diff from fresh Ficoll | | −58.31 | −5.12 | −64.54 | −22.71 | n = 11 donors, 32 replicates

Example 5

Filtration

The feasibility of using back flushed leukocyte filter membranes (PALL Medical) and also the stability of the cells captured on such membranes was investigated at T0 and T24 hours post venipuncture. The captured cells were stored on the membranes in a fridge (2-8° C.) from one donor and RT (18-25° C.) for the second donor. This membrane separation method was performed along side a standard Ficoll PBMC separation method at each time point and temperature.

The membranes that were required to be stored followed steps 1-3 (see below) and then the appropriate storage condition and duration subjected on them. The membrane holder devices were then removed from the storage area and subjected to steps 4-7 (see below) at the relevant time point. The Ficoll control storage samples were kept in the dark at RT and were diluted 1:1 in AIMV cell culture media until required for processing via the standard Ficoll separation method. The membrane procedure is described below:

Steps 1-3 consisted of; 10 ml of WASH BUFFER 1 being filtered through the membrane, using the transfer syringe, into the waste bottle. 10 ml of whole blood sample together with 50 ml of WASH BUFFER 1 was mixed first and then filtered through the LK4 membrane, using the transfer syringe, in to a waste bottle. 50 ml of cooled WASH BUFFER 1 was filtered through the LK4 membrane, using the transfer syringe, into the waste bottle.

Steps 4-7 consisted of: the filter membrane being inverted either immediately or post 24 h (depending on time point). 50 ml of cooled REMOVING BUFFER 1 was filtered back through the membrane, using the back flush syringe, into a 50 ml falcon tube. The cell suspension was spun at 2000 rpm for 5 mins at RT and then re-suspended in 10 mls of AIMV. The cells suspension was again spun at 2000 rpm for 5 mins at RT and then re-suspended in 1 ml of AIMV media and counted according to the standard Ficoll separation method. (WASH BUFFER 1: 500 ml AIMV media buffered with 20 mM HEPES and 1% [w/v] Dextran T40) (REMOVING BUFFER 1: 500 ml AIMV media buffered with 20 mM HEPES and 0.1% [w/v] Dextran T40).

The T-SPOT.TB assay was then performed as indicated in Example 1 and also in the manufactures guidelines accompanying every kit.

The following table describes a summary of results from the T-SPOT.TB tests carried out for this investigation. A comparison of the CEF spot counts with regard to time and temperature of the membrane experiments is shown. This was carried out in terms of the membranes performance in relation to the relevant Ficoll controls carried out on the same day and also their relation at T0.

|  | Date | Donor | Method | Temp | CEF Count (ave, n = 4) | Percentage of Ficoll Control | Percentage of Ficoll control at T0 |
|---|---|---|---|---|---|---|---|
| T0 | Apr. 05, 2006 | 0002 | Ficoll | (RT) | 45.5 | ~ | ~ |
|  |  |  | LK4 | 2-8° C. | 11 | 24.2 | ~ |
|  |  | 0008 | Ficoll | (RT) | 44.4 | ~ | ~ |
|  |  |  | LK4 | RT | 21.25 | 47.9 | ~ |
| T24 | May 04, 2006 | 0002 | Ficoll | (RT) | 47.5 | ~ | 104.4 |
|  |  |  | LK4 | 2-8° C. | 10.5 | 22.1 | 23.1 |
|  |  | 0008 | Ficoll | (RT) | 33.75 | ~ | 76.0 |
|  |  |  | LK4 | RT | 4.75 | 14.1 | 10.7 |

It can be seen from the above table, the membranes used with fresh whole blood, stored at 2-8° C. and 18-25° C. (RT) at both T0 and T24 have provided PBMCs which produce sufficient CEF signal for the use in the ELISPOT assay. The concept of using back flushed filter membranes to harvest PBMCs capable of eliciting a response in the ELISPOT assay has been proven in this case.

Example 6

Storage Time Before Negative Affinity Selection

Two separate experiments were performed, using samples of whole blood from each of 15 donors.

For each experiment: a) on Day 1, immediately after venipuncture, one 10 ml Lithium Heparin Vacutainer of whole blood from each donor was processed ('fresh' samples), according to the standard Ficoll method for PBMC preparation; b) the remaining blood from each donor was stored in the dark, undiluted, in a fridge at 2-8° C. (stored samples) for various times (16 to 72 hours); c) on Day 2, the stored samples were incubated with RosetteSep (StemCell, Vancouver, BC, Canada) as described in Example 4, then processed according to the standard Ficoll method for PBMC preparation. Counting and dilution of PBMC was then carried out, and samples processed, according to Example 4, except that in the two separate experiments performed, one used CEF (5 µg/ml) as antigen, and the other used CEF/PPD (5 µg/ml and 1 µg/ml respectively) in the assay.

The results shown below represent the cumulative SFC counts recorded for all individual donor samples, after each had been subjected to varying processing conditions, using either CEF antigen (n=10) or using both CEF and PPD antigens (n=5), based on summing the mean of the result of three separate ELISPOT assays for each processed sample.

The data demonstrate that samples stored for between 16 and 24 hours at 2-8° C. can subsequently be 'stabilised' with anti-granulocyte antibody prior to being processed with Ficoll, whereas longer storage times followed by the same purification conditions give rise to a gradual reduction in SFC counts in the ELISPOT assay.

|  | Fresh | RosetteSep, Stored at 2-8° C. | | | | |
|---|---|---|---|---|---|---|
| Antigen | Ficoll | 16 hrs | 20 hrs | 24 hrs | 48 hrs | 72 hrs |
| CEF | 940 | 900 | 846 | 892 | 661 | 354 |
| CEF/PPD | 481 | 502 | 476 | 584 | 324 | 108 |

Similar results are obtained when samples are stored at RT for up to 48 hours prior to being 'stabilised' and processed with Ficoll.

Example 7

Negative Affinity Selection Using Anti-CD15 Magnetic Beads

Two separate experiments were performed, using samples of whole blood from each of 8 donors. The blood was collected into 6 ml Lithium Heparin Vacutainers. Cells were separated from whole blood using either (i) Negative Affinity Selection or (ii) Ficoll.

(i) Negative Affinity Selection. 4 ml of blood from each donor was processed immediately after collection ('fresh' samples) using the Negative Affinity Selection procedure described below; the remainder was stored at RT, and 4 ml of blood from each donor processed after either 24 hours or 48 hours of storage.

At each time point 4 ml of whole blood was added to 36 ml cold Ammonium Chloride Lysis Solution (8.26 g/L Ammonium Chloride, 1.0 g/L Potassium bicarbonate, 0.037 g/L EDTA, pH 7.2-7.6), mixed and incubated at 2°-8° C. for 15 minutes. The samples were centrifuged at 300×g for 5 minutes, the supernatant removed, and the cells re-suspended in 10 mls wash buffer (PBS, 2 mM EDTA, 0.5% BSA). The samples were centrifuged again at 300×g for 5 minutes, and the supernatant removed. The cells were re-suspended in 80 μl wash buffer. 20 μl of CD15 MicroBeads (Miltenyi Biotech) to label granulocytes, and 20 μl CD235a MicroBeads (Miltenyi Biotech) to label residual RBC, were added to each sample. Samples were mixed and incubated for 15 minutes at 2°-8° C. 2 mls wash buffer was added, and samples centrifuged for 5 minutes at 300×g. The supernatants were removed and each cell pellet was re-suspended in 500 μl of wash buffer. These labelled samples were then depleted using LD MACS cell separation columns according to the manufacturer's instructions (Miltenyi Biotech). The unlabelled cells were collected from the columns, centrifuged to pellet, and re-suspended in 1 ml AIM V medium.

(ii) Ficoll. In parallel, using the standard Ficoll method (see Example 1), 4 ml of blood from each donor was processed immediately after collection ('fresh' samples); the remainder was stored at RT, and 4 ml of blood from each donor was processed after either 24 hours or 48 hours of storage. Cells collected were re-suspended in 1 ml AIM-V medium.

At each time point, cells collected from each of the cell isolation procedures were counted and diluted in AIM-V to give 250,000 cells/100 μA All samples were then assayed in the T-SPOT.TB assay as outlined in Example 1 using CEF (Mabtech, 0.66 μg/ml) as antigen. FIG. 1 below shows the data obtained from 4 representative donors of the 8 donors tested.

The data shows that the blood samples processed with Negative Affinity Selection, using anti-CD15, after 48 hours storage gives similar spot counts to samples prepared using Ficoll with blood processed within 8 hours of collection.

What is claimed is:

1. In an improved method of performing a cell-mediated immunoassay that measures an antigen-specific cytokine response of T cells present in a whole blood sample which has been collected from a subject and maintained in vitro for at least 8 hours after said collection, the improvement comprising (i) purifying a population of cells comprising lymphocytes and antigen presenting cells from said maintained sample by a process comprising a positive or negative affinity selection step in order to remove granulocytes; and (ii) using said population of cells in the cell-mediated immunoassay to measure the antigen-specific cytokine response of T cells.

2. The method of claim 1, wherein said sample is maintained for between 12 and 36 hours after said collection.

3. The method of claim 1, wherein said sample is maintained for between 12 and 48 hours after said collection.

4. The method of claim 1, wherein said sample is maintained for between 24 and 48 hours after said collection.

5. The method of claim 1, wherein said sample is maintained between 2-8° C.

6. The method of claim 1, wherein said sample is maintained between 18-25° C.

7. The method of claim 1, wherein said cell-mediated immunoassay measures an antigen-specific cytokine response in immediate effector T cells.

8. The method of claim 1, wherein the step (i) of purifying comprises a negative affinity selection step wherein said maintained sample is contacted with an antibody preparation comprising anti-CD66b and glycophorin A antibodies to aggregate red blood cells and granulocytes, and said aggregated red blood cells and granulocytes are removed from said maintained sample by centrifugation.

9. The method of claim 1, wherein granulocytes are removed in the step (i) of purifying by contacting said maintained sample with a solid support comprising an anti-CD15 ligand to remove CD15+ cells from said maintained sample.

10. The method of claim 9, wherein said solid support further comprises magnetic beads, and wherein the step (i) of purifying further comprises contacting said maintained sample with said beads to bind CD15+ cells to said beads, and separating said beads having said CD15+ cells bound thereto from said maintained sample.

11. The method of claim 9, wherein red blood cells in said maintained sample are removed by lysis or filtration, prior to step (ii).

12. The method of claim 1, wherein said purification leads to an increase in the sample of both the ratio of T cells to total cells and the ratio of antigen presenting cells to total cells.

13. The method of claim 1, wherein said sample is not frozen before said purification.

14. The method of claim 1, wherein said purified cells are not frozen before said use.

15. The method of claim 1, wherein the step (i) of purifying comprises a positive affinity selection step.

16. The method of claim 15, wherein said positive affinity selection step selects all types of T cells.

17. The method of claim 15, wherein the step (i) of purifying comprises contacting said maintained sample with a solid support having attached thereto ligands, wherein said ligands bind to cell surface proteins present on the surface of said lymphocytes and antigen presenting cells, and wherein said lymphocytes and antigen presenting cells are bound to said solid support via said ligands.

18. The method of claim 17, wherein said solid support comprises one or more ligands selected from anti-CD4, anti-CD8, anti-CD19 and anti-CD14 ligands to purify CD4+, CD8+, CD19+ or CD14+ cells from said maintained sample.

19. The method of claim 17, wherein said bound lymphocytes and antigen presenting cells are separated from said solid support before said use in step (ii).

20. The method of claim 17, wherein said bound lymphocytes and antigen presenting cells are retained on said solid support before said use in step (ii).

21. The method of claim 17, wherein said solid support comprises magnetic beads.

22. The method of claim 21, wherein each said magnetic bead has bound thereto anti-CD4, anti-CD8 and anti-CD19 ligands.

23. The method of claim 21, wherein each magnetic bead has bound thereto one or more ligands selected from anti-CD4, anti-CD8 and anti-CD19 ligands, and wherein said beads are mixed together to provide said solid support for binding to CD4+, CD8+ and CD19+ cells.

24. The method of claim 15, wherein red blood cells in said maintained sample are removed by lysis or filtration, prior to step (ii).

25. The method of claim 1, wherein said cell-mediated immunoassay is an ELISPOT assay.

26. The method of claim 1, wherein said subject is a human.

27. The method of claim 1, wherein the step of maintaining the whole blood sample includes shipping or transporting said sample from one geographical location to another.

28. The method of claim 26, wherein said cell-mediated immunoassay is to diagnose or monitor a disease.

29. The method of claim 1, wherein said sample is maintained for up to 12 hours after said collection.

30. The method of claim 1, wherein said sample is maintained for up to 18 hours after said collection.

31. The method of claim 1, wherein said sample is maintained for up to 24 hours after said collection.

32. The method of claim 1, wherein said sample is maintained for up to 36 hours after said collection.

* * * * *